Figure 3:
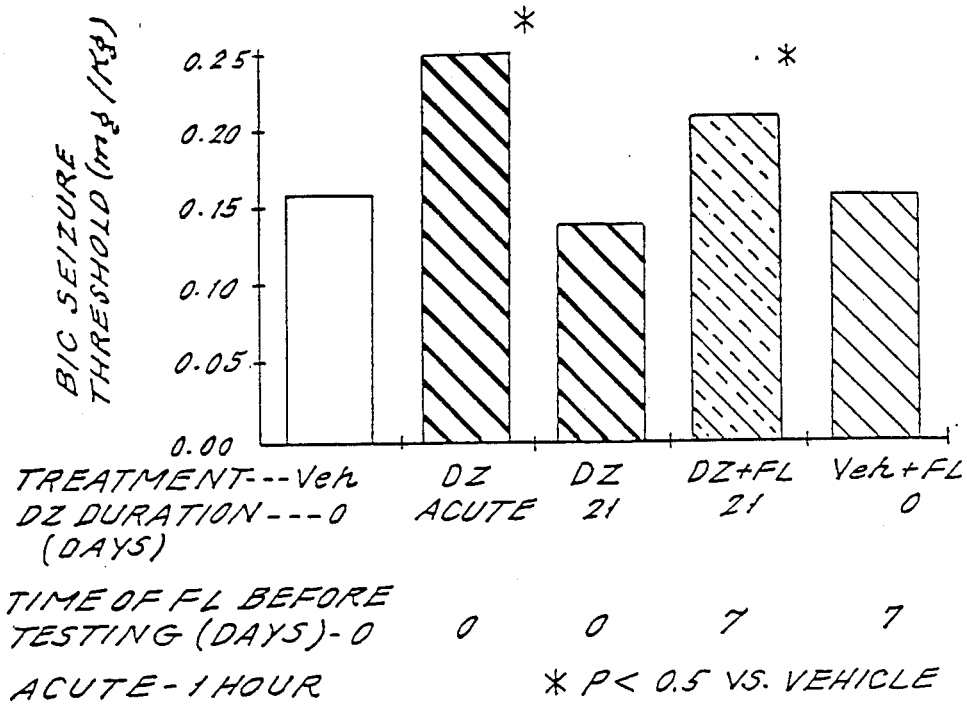

United States Patent [19]

Gallager

[11] Patent Number: 4,666,903

[45] Date of Patent: May 19, 1987

[54] NOVEL USE OF BENZODIAZEPINE ANTAGONIST

[75] Inventor: Dorothy W. Gallager, Guilford, Conn.

[73] Assignee: Yale University, New Haven, Conn.

[21] Appl. No.: 765,257

[22] Filed: Aug. 13, 1985

[51] Int. Cl.$^4$ ............................................. A61U 31/55
[52] U.S. Cl. ..................................................... 514/220
[58] Field of Search ........................................ 514/220

[56] References Cited

PUBLICATIONS

Chem. Abst. 97-138502(Z), 104,176(F) & 174930(W), (1982).

Sandra E. File, "Recovery from Lorazepam Tolerance and the Effects of a Benzodiazepine Antagonist (RO 15-1788) on the Development of Tolerance," Psychopharmacology (1982) 77:284-288.

Scott E. Lukas, Roland R. Griffiths, "Precipitated Withdrawal by a Benzodiazepine Receptor Antagonist (RO 15-1788) After 7 Days of Diazepam", Science, vol. 217, 17 Sep. 1982.

L. F. McNicholas and W. R. Martin, "The Effect of a Benzodiazepine Antagonist, RO15-1788, In Diazepam Dependent Rats," Life Sciences, vol. 31, pp. 731-737.

R. J. Lamb and R. R. Griffiths, "Effects of Repeated Ro 15-1788 Administration in Benzodiazepine-Dependent Baboons", European Journal of Pharmacology, vol. 110, No. 2, pp. 257-261.

*Primary Examiner*—Stanley J. Friedman
*Attorney, Agent, or Firm*—Ostrolenk, Faber, Gerb & Soffen

[57] ABSTRACT

Benzodiazepine antagonists are used to regenerate the sensitivity response to and prevent tolerance of benzodiazepine which otherwise develops during chronic benzodiazepine exposure. The administration of a plurality of time spaced doses of the antagonist also prevents benzodiazepine withdrawal symptoms. The preferred benzodiazepine antagonist is flumazepil.

3 Claims, 4 Drawing Figures

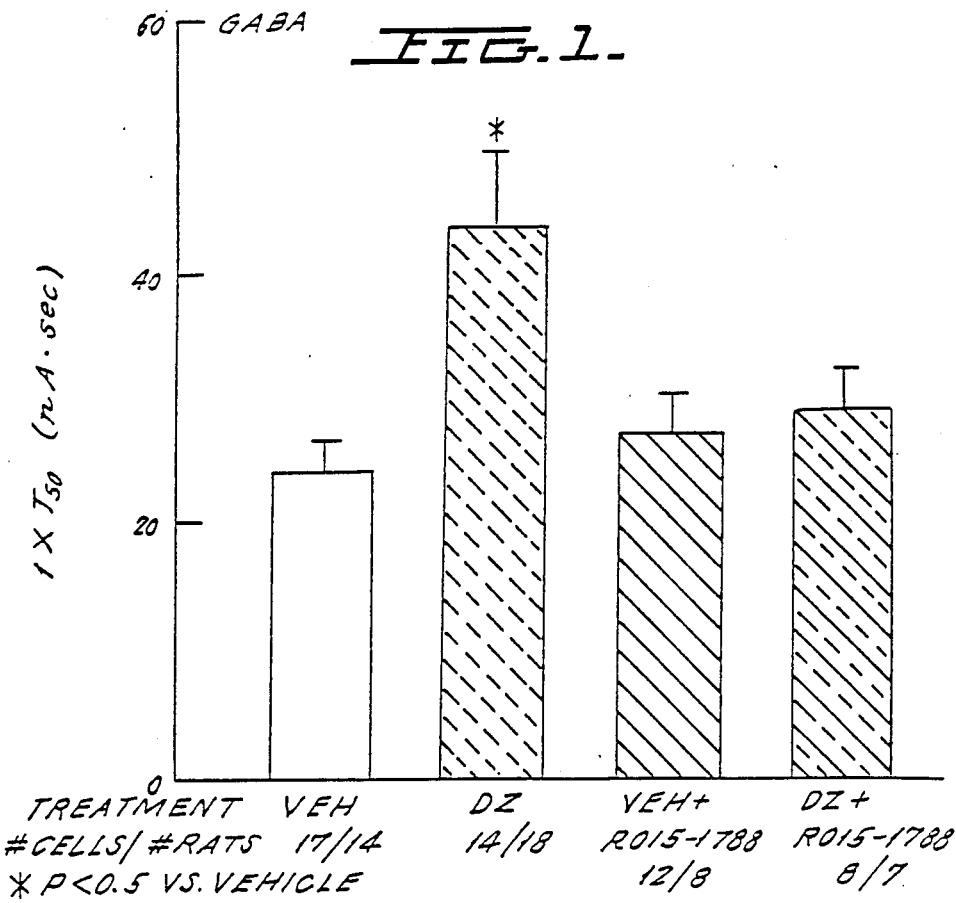
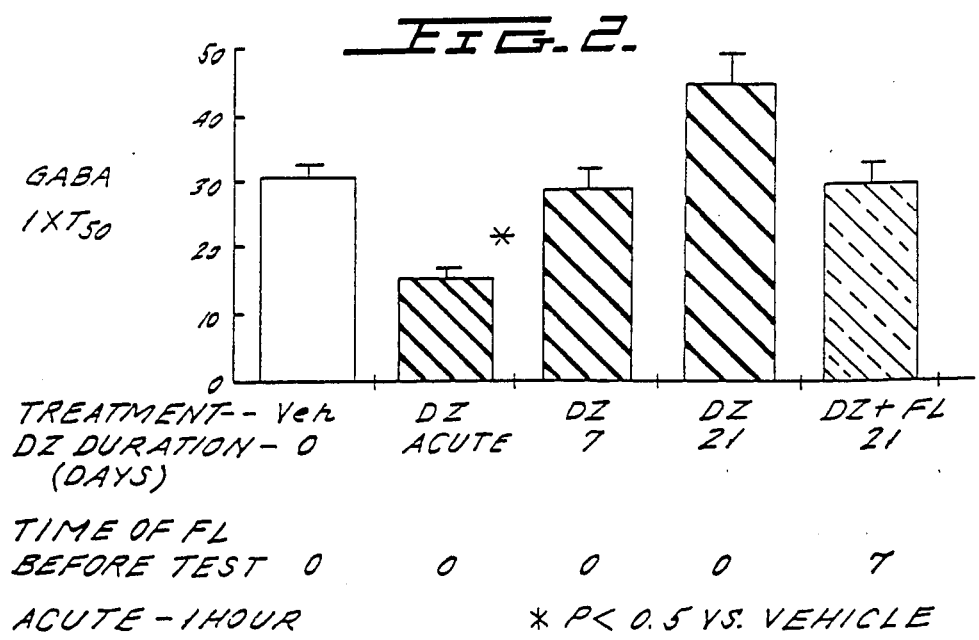

NOVEL USE OF BENZODIAZEPINE ANTAGONIST

This invention was made with government support under grant NINCDS RO1 N519655 from the NIH. The U.S. government has certain rights in this invention.

BACKGROUND OF THE INVENTION

For many years, barbiturates were the most commonly used drugs in the treatment of symptomatic anxiety. The discovery of the benzodiazepine nucleus by Sternbach and his colleagues led to the development of chlordiazepoxide, the first member of a group, which was shown to be highly effective with few side effects. Within a few years of their introduction in 1960, the benzodiazepines have effectively replaced barbiturates as the drugs of choice in anxiety and insomnia and their additional use as anti-convulsants and muscle relaxants added to their clinical and commercial potential.

The benzodiazepines exert most of their pharmacological effects by a selective facilitation of the postsynaptic actions of gamma-aminobutyric acid (hereinafter "GABA"). A number of clinical, behavioral and electrophysiological studies have demonstrated that the chronic administration of benzodiazepines, results in tolerance to the sedative, muscle relaxant and anticonvulsant properties of the drug. Although the cellular basis for these behavioral changes is not well understood, present knowledge of benzodiazepine receptor functions points to involvement of GABAergic processes. It is well known, for example, that acutely administered benzodiazepines selectively enhance postsynaptic GABAergic neurotransmission. However, prolonged exposure to benzodiazepines in vivo and in vitro markedly attenuates this facilitory effect. Classic tolerance is normally followed by escalation in dosage to maintain the drug's pharmacological effects. An escalation in dosage, however, is undesirable.

Upon development of tolerance, the continued administration of the benzodiazepines is not beneficial. The cessation of administration, however, often leads to withdrawal syndrome. The first symptoms experienced in a withdrawal syndrome are identical to those of anxiety, including apprehension, somatic complaints such as nausea and palpitations and tension. It has been known for many years that patients often experience anxiety after reduction of benzodiazepine intake. The withdrawal reaction develops into a characteristic abstinence syndrome with specific symptoms which cannot be explained by anxiety alone. The time course of each condition also differs. When a drug is stopped, symptoms can remain as they are (neutral reaction), become steadily worse after withdrawal until they reach a plateau of higher symptomatology (anxiety reactions) or increase temporarily before returning to their original level (withdrawal reaction).

When benzodiazepines that have been taken long term in regular dosage are stopped, there is a variable period of hours to several days before adverse effects appear. This variability occurs because of the accumulation of benzodiazepine drugs and their active metabolites during the long-term administration. The amount of accumulation with multiple dosage depends on the elimination half life of the drug and its metabolites, being less with the compounds of short half life. The period of onset of withdrawal reactions is therefore dependent on the drug half life. The duration of the withdrawal reaction is also variable and can last up to twenty days. The temporary prescription of other drugs, particularly beta blockers, may attenuate the withdrawal symptoms.

As is apparent, there is a continuing need for an effective agent which will prevent benzodiazepine withdrawal symptoms and a continuing need for an agent which will regenerate the sensitivity response to and prevent tolerance of benzodiazepines which are chronically administered.

The need for a drug which could reverse some or all of the effects of benzodiazepines has occasionally been expressed by clinicians. Indications proposed for such an "antidote" include the selective reduction of the sedative effects in patients who require high doses of benzodiazepines for the treatment of severe muscular spasticity, the reversal of sedation and anterograde amnesia in surgical patients operated on using balanced anesthesia containing benzodiazepines and from whom informed consent is required for an urgent subsequent surgical intervention, the treatment of accidental overdosages in children and the treatment of suicidal intoxication in adults. As a result of the perceived need, a series of benzodiazepine antagonist have been developed. See, e.g., Haefley et al, Benzodiazepines Antagonists, The Benzodiazepine: From Molecular Biology to Clinical Practice (Costa, Ed. Raven Press, New York, 1983), pp. 137-146. A particularly effective benzodiazepine antagonist is flumazepil, ethyl-8-fluoro-5,6,dihydro-5-methyl-6-oxo-4H-imidazo [1,5a](1,4)benzodiazepine-3-carboxylate; also known as Ro 15-1788. See, e.g., Darragh et al, Absence of Central Effects in Man of the Benzodiazepine Antagonist Ro 15-1788, Pharmacology (1983) 80: 192-195 and Klotz et al, Pharmakinetics of the Selective Benzodiazepine Antagonist Ro 15-1788 in Man, Eur. J. Clinic. Pharmacol. (1984) 27:115-117.

In an article that I co-authored with J.M. Lakoski, S. F. Gonsalves and S. L. Rauch, Chronic Benzodiazepine Treatment Decreases Postsynaptic GABA Sensitivity, Nature, Vol. 308, No. 5954, pp. 74-77, Mar. 1, 1984, we point out that acute injection of flumazepil reversed rapidly the decrease in GABA sensitivity observed in chronically diazepam treated animals without altering GABA sensitivity in vehicle treated animals. Since flumazepil is well known to have an extremely short half life, on the order of about 15 minutes in rats, it was believed that the reversal was transitory and very short lived. In humans, flumazepil has a half life of approximately 1 hour (Klotz, et al, 1984). By way of comparison the benzodiazepine agonist, triazolam, has an elimination half life of 2-5 hours and is considered to have an ultra short half life when compared to other benzodiazepines.

I have now determined that a single exposure to benzodiazepine antagonists like flumazepil actually reverses benzodiazepine tolerance completely and persistently, an event which is correlated with an alteration in the GABA receptor complex back to its pre-drug state. This is different from direct antagonism at the benzodiazepine receptor site which occurs when sufficient quantities of antagonists are present in the system to competitively displace the agonist (i.e. the benzodiazepine). It is believed that tolerance to benzodiazepines is due to an alteration in the GABA-benzodiazepine receptor complex and that the antagonist shifts the altered complex back to its normal, agonist-native state. Since tolerance develops over a protracted time period, effective clinical prevention of tolerance can be achieved by the periodic exposure to antagonist during the course of active benzodiazepine exposure before significant tolerance develops. It has also been determined that such periodic administration of the antagonist prevents withdrawal lability. In seizure disorders in which chronic benzodiazepine administration is efficacious but limited by tolerance development, the periodic administration of the antagonist would allow continued effective treatment with the benzodiazepines a would the anti-spastic effects following chronic benzodiazepine treatment. In panic disorders, where some benzodiazepine analogs have been shown to be efficacious, periodic administration of antagonists would prevent tolerance development and withdrawal lability.

Figure 4:
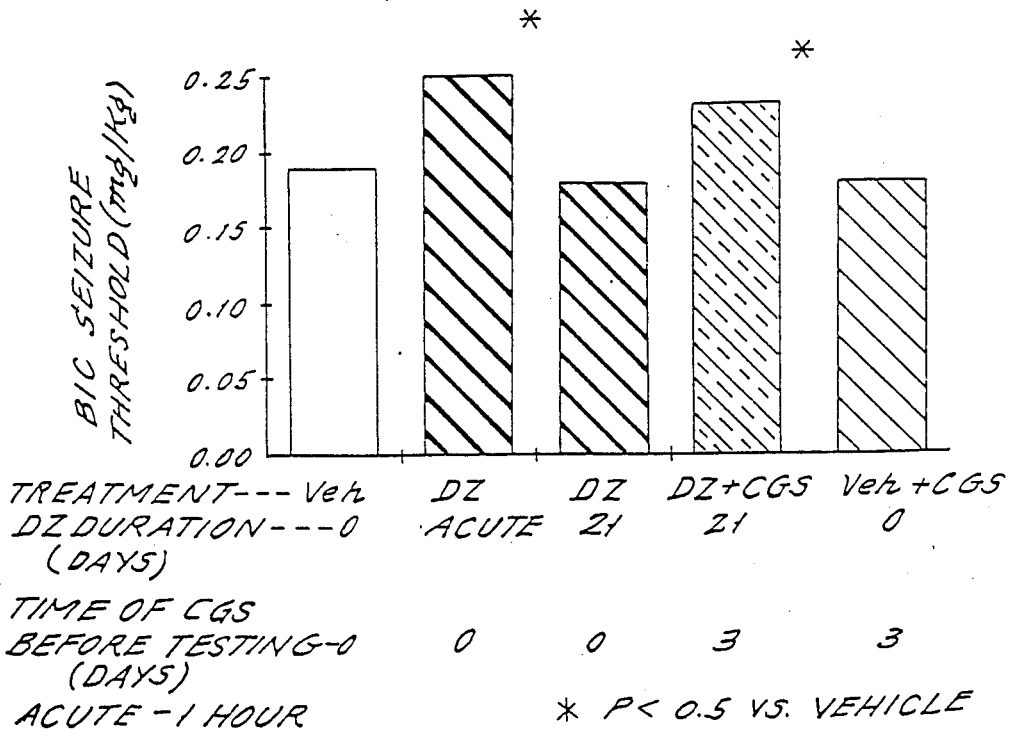

It is, accordingly, the object of this invention to provide a method for regenerating sensitivity of response and thereby preventing tolerance to benzodiazepines, particularly during chronic benzodiazepine and also to provide a method of preventing benzodiazepine withdrawal symptoms. These and other objects of the invention will be apparent to those skilled in the art from the following detailed description in which FIGS. 1 and 2 are histograms of mean $IxT_{50}$ values and FIGS. 3 and 4 are histograms of bicuculline seizure threshold values.

SUMMARY OF THE INVENTION

This invention relates to a method of regenerating sensitivity of response to and preventing tolerance to benzodiazepines, particularly during chronic benzodiazepine administration and also to preventing benzodiazepine withdrawal symptoms. More particularly, the invention provides a method of regenerating response to benzodiazepines by periodically administering a benzodiazepine antagonist to a benzodiazepine recipient prior to the establishment of benzodiazepine tolerance. The periodic administration of benzodiazepine antagonist also prevents benzodiazepine withdrawal symptoms.

DESCRIPTION OF THE INVENTION

In accordance with the present invention, a method of regenerating sensitivity of response to and preventing tolerance to benzodiazepines is provided and involves the periodic administration to a benzodiazepine recipient, prior to establishment of benzodiazepine tolerance by the recipient, of an effective sensitivity regenerating amount of a benzodiazepine antagonist. The periodic administration of the antagonist also prevents benzodiazepine withdrawal symptoms.

The benzodiazepines are a well known class of drugs. Some of the currently available benzodiazepines are alprazolam, lorazepam, lormethazepam, oxazepam, temazepam, triazolam, bromazepam, chlordiazepoxide, chlobazam, clorazapate, diazepam, flunitriazepam, flurazepam, ketazolam, medazepam, nitrazepam and prazepam. These compounds, their preparation and use are well known and will not be described further in this specification. Use of some of these benzodiazepines is long term (i.e. chronic).

Beta-carbolines, such as propyl-beta-carboline, pyrazoloquinoline, CGS-8216, and imidazobenzodiazepines such as flumazepil, (Ro 15-1788) are benzodiazepine antagonists whose structure, preparation and use are known. The present invention employs these antagonists formulated in the same manner and used in the same amounts, as such materials are used as competitive antagonists. For example, in the rodent studies, the amounts that are used for preventing tolerance development are the same as the amounts reported to be the $ED_{50}$ values for inhibiting benzodiazepine binding to brain receptors as outlined in an article by Braestrup and Nielson, (Handbook of Psychopharmacology, 17: 285-384, 1983). The particular amount of the antagonist employed in accordance with the present invention and the time interval between administrations depends on the identity of the antagonist selected and the identity of the benzodiazepine which the individual is receiving. This amount, therefore, is best determined by the attending clinician with the compound which I suggest to be the preferred antagonist, flumazepil. For this drug, the dosage will generally be about 3–5 mg/kg as described in the primate studies from the preliminary studies listed in my laboratory and those listed in baboon studies by Dr. Griffiths, i.e. Lamb and Griffiths, 1984 and Lukas and Griffiths 1982. The dosage to be about 3–5 mg/kg, the time interval about 1–3 days for regeneration purposes and about 1–3 days for attentuation purposes.

The time course for spontaneous and flumazepil-induced reversal of GABAergic subsensitivity (i.e., tolerance) measured electrophysiologically was examined following the termination of a chronic benzodiazepine treatment protocol in which rats were given daily injections of diazepam (5 mg/kg) for 21 days. The decreased responsiveness to GABA persisted for up to 96 hours after the final dose of injected diazepam even though the agonist and its active metabolites could not be detected in brain tissue by 24 hours after the last administration. When the chronic benzodiazepine treatment is by means of a continuous release procedure, the withdrawal is even more protracted, lasting at least 120 hours after drug discontinuation. Animals tolerant to the effects of the benzodiazepines characteristically show little or no GABAergic facilitation in response to subsequent doses of the agonist.

Rats were administered flumazepil (4 mg/kg, ip) or its vehicle (0.1% Tween 80 with 0.2% carboxymethyl cellulose) on the final day of chronic diazepam (average dose 1.1 mg/kg, iv) or vehicle treatment, 22 hours prior to electrophysiological determinations in accordance with Gallager, Benzodiazepines: Potentiation of a GABA Inhibitory Response in the Dorsal Raphe Nucleus, Eur. J. Clin. Pharmacol. 49: 133 (1978) and Gallager, et al, Failure of Chronic Lithium Treatment to Block Tricyclic Antidepressant-Induced 5-HT Supersensitivity, Naunyn-Schmiedeb. Arch. Pharmacol., 307: 129 (1979). FIG. 1 is a histogram showing mean $IxT_{50}$ values ($\pm$SEM) for data pooled from three series of experiments conducted 3-6 months apart.

Chronic diazepam administration causes a significant increase in the amount of GABA required to inhibit neuronal activity (subsensitivity), as shown in FIG. 1, bar 2. The data demonstrate that the acute administration of the antagonist (Ro 15-1788 +DZ) reverses subsensitivity persistently (bar 4). Since the half life of the flumazepil in the rat brain is only 16-20 minutes, it is unlikely that this reversal merely represents competitive antagonist displacement of the agonist. It is believed that the antagonist alters in some way the conformation of the GABA/benzodiazepine macromolecular complex such that the GABA recognition site is restored to its native low affinity state. An additional single dose of diazepam given 16 hours after the flumazepil administration did not reinstate the GABAergic subsensitivity.

In other experiments, diazepam was administered by continuous release capsules (silastic tubing filled with crystalline diazepam) implanted in rats for a total of 7 days or 21 days and maintaining an equivalent daily dose of 5 mg/kg of diazepam. At the end of this treatment period, electrophysiological recordings were undertaken to determine GABA sensitivities; diazepam levels were maintained throughout the recording period by the continued presence of the diazepam capsules. For comparison, a single acute dose (1 mg/kg,i.v.) of diazepam is shown to produce a significant decrease in GABA IxT$_{50}$ under similar recording conditions (second bar, FIG. 2). At 7 days after diazepam implantation, no change in GABA sensitivity is evident (bar 3). However, a significant increase in GABA IxT$_{50}$ is apparent 21 days after implantation (bar 4), suggesting that significant tolerance develops between 8 and 21 days after the implantation. Flumazepil was than administered (4 mg/kg) by means of a single i.p. injection 7 days prior to the electrophysiological recording session, i.e. 14 days after capsule implantation (bar 5). The flumazepil administration resulted in GABA sensitivities in the control range. This demonstrates that the antagonist reversed the effects of chronic diazepam on GABA sensitivity and had a persistent effect since one would anticipate continued development of tolerance (subsensitivity to GABA) if only reversible competitive displacement were occurring.

An examination of changes in seizure threshold indicates that following chronic diazepam treatment, a single i.p. injection of a imidazobenzodiazepine, flumazepil, (4 mg/kg) 7 days prior to bicuculline seizure threshold determination restores the anticonvulsant efficacy of diazepam in rats chronically implanted with diazepam releasing capsules (FIG. 3). Similarly, a single i.p. injection of the pyrazoloquinoline, CGS8216, in a dose of 1 mg/kg, 3 days prior to seizure threshold determination, also restores the anticonvulsant efficacy of diazepam in rats chronically implanted with diazepam releasing capsules (FIG. 4). Because the reversal of tolerance is achieved by a pryazoloquinoline (CGS-8216), as well as an imidazobenzodiazepine (flumazepil), it is apparent that the chemical nature of the antagonist is not restrictive, rather it is the property of being an antagonist. However, the longer half-life of CGS-8216 (19 hr in the rat) makes antagonists like flumazepil more suitable for this application.

An experiment was conducted to examine the prevention of withdrawal behavior in primates using six Rhesus monkeys of both sexes. (See Table 1). Monkeys received diazepam in two daily im injections (8 AM and 6 PM) in total daily doses of 1.5 or 3.0 mg/kg as listed in table 1 for 9 or 12 consecutive days. Monkeys 2,5 and 6 received in addition, an im injection of flumazepil (5 mg/kg, im) on every third day of the diazepam treatment. At the end of the chronic diazepam treatment period, all of the monkeys received an injection of flumazepil (5 mg/kg, im) and severe withdrawal symptoms were rated for each monkey from video tapes recording reactions for 3 hours following antagonist administration. As can be seen in Table 1, retching and vomiting was observed in every monkey on chronic diazepam alone (Monkeys #1,3, and 4; 3 out of 3 monkeys) following flumazepil. However, retching and vomiting were never observed in monkeys treated periodically with flumazepil in addition to receiving chronic diazepam (monkeys #2,5 and 6; 0 out of 3 monkeys, Table 1). A subsequent injection of flumazepil, administered 1 day following the initial withdrawal, failed to elicit withdrawal symptoms in any monkey in either treatment protocol (0 out of 6 monkeys, Table 1). Although incomplete, a crossover of treatments for monkeys on the two treatment protocols is being carried out. Monkey #1 when switched to periodic flumazepil, failed to vomit or retch after receiving the test dose of antagonist despite concommitant continuation of diazepam treatment for 9 days. However, Monkey #2 also failed to show vomiting and retching when switched to chronic diazepam treatment alone for 9 additional treatment days. Thus when rated for withdrawal symptoms (vomiting and retching) 3 out of 4 monkeys (including crossover) showed symptoms after drug-induced withdrawal following 9–12 days of continuous diazepam treatment. By comparison, 0 out of 4 monkeys (including crossover) showed no vomiting or retching after drug-induced withdrawal when flumazepil was periodically administered during the diazepam treatment.

The study just described demonstrates that periodic administration of the benzodiazepine antagonist had prevented severe withdrawal symptoms (vomiting and retching) in primates.

Various changes and modifications can be made in the process of the present invention without departing form the spirit and scope thereof. The various embodiments described herein were for the purpose of further illustrating the invention but were not intended to limit it.

TABLE 1

| Monkey # | Sex | Weight (kg) | Chronic Treatment | | | Withdrawal Symptoms* (vomiting and retching) | |
|---|---|---|---|---|---|---|---|
| | | | Diazepam (mg/kg/day) | Duration (days) | Flumazepii (mg/kg/3rd day) | First Day | Second Day |
| 1 | F | 6.3 | 1.5 | 9 | 0 | yes | no |
| 2 | F | 5.2 | 1.5 | 9 | 5 | no | no |
| 3 | M | 11.1 | 3.0 | 12 | 0 | yes | no |
| 4 | F | 7.9 | 3.0 | 12 | 0 | yes | no |
| 5 | M | 9.2 | 3.0 | 12 | 5 | no | no |
| 6 | M | 11.0 | 3.0 | 12 | 5 | no | no |

*elicited by a single i.m. injection of flumazepil (5 mg/kg) administered on 2 consecutive days at the end of chronic diazepam treatment.

What is claimed is:

1. A method of regenerating sensitivity of response to, and preventing tolerance and withdrawal lability of benzodiazepines, which comprises administering to a benzodiazepine recipient who has been receiving chronic benzodiazepine treatment, but prior to establishment of benzodiazepine tolerance and withdrawal lability by said recipient, an effective sensitivity regenerating amount of flumazepil at time spaced intervals during said chronic treatment, but separate from the time of administration of the benzodiazepine agonist.

2. The method of claim 1 in which the time spaced intervals are about 1 to 3 days.

3. The method of claim 1 in which the time spaced intervals are at least about one day.

* * * * *